United States Patent [19]

Quenin et al.

[11] Patent Number: 4,931,257

[45] Date of Patent: Jun. 5, 1990

[54] POSITIVELY ENGAGED PIPETTE AND PIPETTE SUPPORT

[75] Inventors: John A. Quenin, Rochester; Johannes J. Porte, Webster, both of N.Y.

[73] Assignee: Eastman Kodak Company, Rochester, N.Y.

[21] Appl. No.: 293,713

[22] Filed: Jan. 5, 1989

[51] Int. Cl.$^5$ ............................ B01L 3/02; B01L 9/00
[52] U.S. Cl. .................................... 422/100; 422/104; 422/63; 73/864.14; 248/221.4
[58] Field of Search .................... 422/100, 63, 104; 73/864.01, 864.14, 864.16, 864.17, 864.18; 248/222.4, 223.1, 221.4, 310, 408, 414

[56] References Cited

U.S. PATENT DOCUMENTS

| 3,696,974 | 10/1972 | Van der Veken | 73/864.63 X |
| 4,557,619 | 12/1985 | DeVincentis | 401/287 X |
| 4,773,815 | 9/1988 | Lemelson | 901/29 X |
| 4,798,705 | 1/1989 | Jakubowicz | 422/104 X |

FOREIGN PATENT DOCUMENTS 278144 8/1988 European Pat. Off. .

Primary Examiner—Michael S. Marcus
Assistant Examiner—Jeffrey R. Snay
Attorney, Agent, or Firm—Dana M. Schmidt

[57] ABSTRACT

Means are described for positively engaging a key in a keyway in a pipette and its support, to insure that proper dispensing position is maintained and that the pipette stays in the support. Preferably spring means are provided on the key for pressing against the keyway.

12 Claims, 3 Drawing Sheets

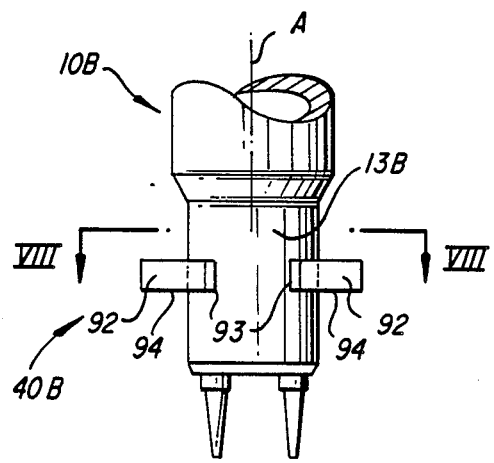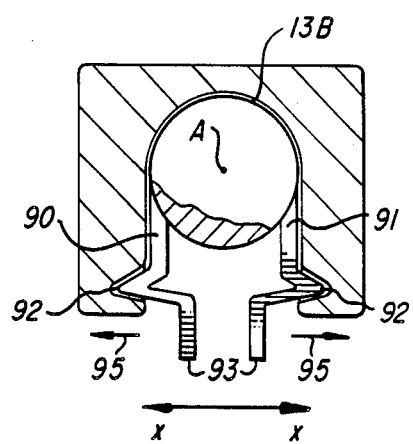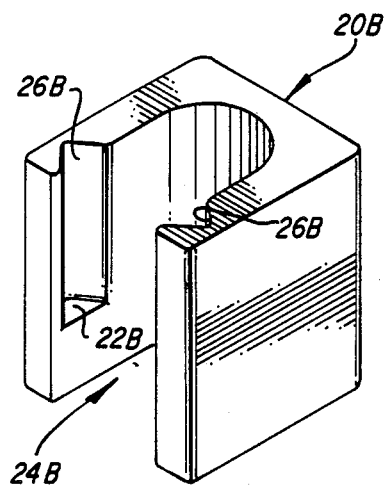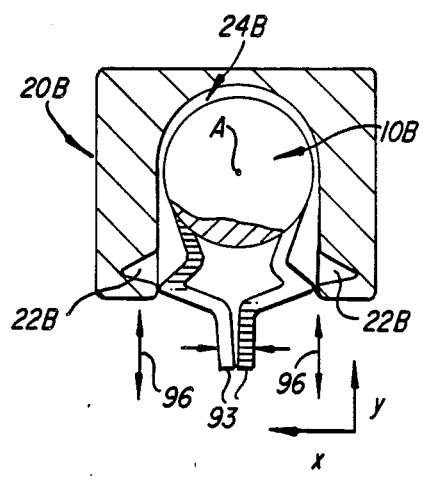

POSITIVELY ENGAGED PIPETTE AND PIPETTE SUPPORT

FIELD OF THE INVENTION

This invention relates to a pipette and a support for that pipette.

BACKGROUND OF THE INVENTION

Pipettes are used in conventional blood analyzers, by placing them in a support that fixes them relative to a test element onto which liquid is to be dispensed. That is, the dispensing tip of the pipette needs to be at a nonvarying predetermined distance from the test element, and appropriately centered, during the dispensing step. The conventional support has featured a stand having an aperture therein which preferably includes a keyway, and a key on the pipette is designed to loosely fit within the keyway. A tight fit is not needed, since gravity maintains the pipette against a stop to achieve the desired vertical height from the test element, and only gross rotational misadjustment and the X-Y plane need be prevented by the key and keyway interaction. An example of such a pipette and pipette support is shown in EPO Publication No. 278,144.

Such pipette supports normally are quite satisfactory and effective. However, because they do rely on gravity to fix the pipette in the "Z", or vertical, direction, they are insufficient when used in microgravity or zero gravity environments, such as in a space station. That is, the loose fit of the pipette along the Z axis within the pipette stand means that any accidental jarring can cause the pipette to (a) leave its stop and lose the desired "height" distance, that is, the distance from the test element, not to mention (b) leave the vicinity of the support entirely as a flying object.

Furthermore, even in 1 G environments the loose fitting support can still provide too much potential misadjustments, particularly if tolerances are not followed during manufacturing, or if the chemistries being analyzed require unusually accurate positioning of the pipette, or if greater accuracy of analysis is desired. Close tolerances are too costly to maintain anyway, so the risk of a sloppy fit always remains.

Thus, there has been a need, prior to this invention, to have a pipette support that more positively engages the pipette.

SUMMARY OF THE INVENTION

We have constructed pipette support means for positively engaging a pipette within the support, to prevent its movement away from a test element on which liquid is to be dispensed.

More specifically, there is provided a pipette and a support for the pipette that include a keyway on one and a mating key on the other, the support further including stop means against which the pipette is placed to dispense liquid onto a test element from a predetermined distance and location. This is improved in that the key and keyway include holding means for releasibly holding the key in the keyway and the pipette within the support and against the stop, to prevent accidental pipette movement that would alter the predetermined distance or location from the test element.

Accordingly, it is an advantageous feature of the invention that a pipette constructed in accord with the invention is positively engaged within its support, so as to require more than accidentally applied force to mislocate it from its ideal location or to remove it from the stop that determines the predetermined dispensing height.

It is a related advantageous feature of the invention that such a pipette and its support can be used in micro or zero gravities without fear of the pipette inadvertently disengaging the pipette support.

Other advantageous features will become readily apparent upon reference to the following Description of the Preferred Embodiments, when read in light of the attached drawings.

BRIEF DESCRIPTION OF THE DRAWINGS

FIG. 7 is a view similar to that of FIG. 1, illustrating yet another embodiment;

FIG. 8 is a section view taken generally along line VIII—VIII of FIG. 7, but with the pipette in place in the pipette support;

FIG. 9 is an isometric view of the pipette support of FIG. 8; and

FIG. 10 is a section view similar to that of FIG. 8, but illustrating the pipette being moved in or out of the support aperture.

DESCRIPTION OF THE PREFERRED EMBODIMENTS

The invention is described in connection with a pipette and pipette support as used with a biological fluids analyzer, in which the pipette is a dual pipette and the key is on the pipette, the keyway being in the support. In addition, the invention is useful regardless of (a) what equipment, if any, the pipette support is part of, (b) whether it is a dual pipette or not, and (c) regardless whether the key is on the pipette or support (the keyway being in the other of the two).

Figure 1:
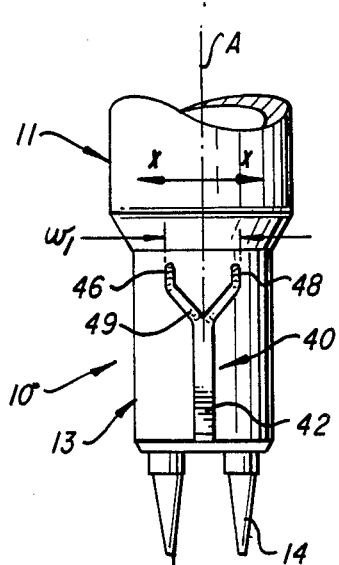
FIG. 1 is a fragmentary front elevational view of a pipette constructed in accordance with the invention.
Figure 2:
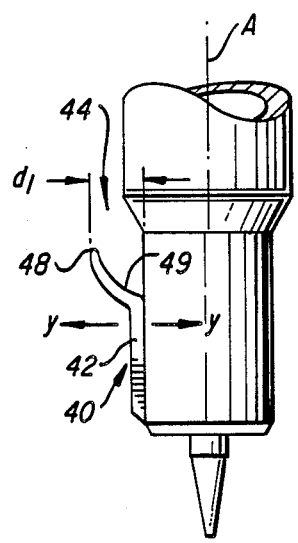
FIG. 2 is a fragmentary side elevational view of the pipette of FIG. 1.

Turning now to FIG. 1, a conventional dual pipette 10 is shown, except that its interior mechanism is not shown, since it can be either manually operated or automatic. It has an upper body portion 11 and a lower body portion 13. Twin tips 12, 14 are used to dispense liquid onto a conventional, preferably dried test element E, FIG. 3. The pipette has a long axis A, as is conventional.

To maintain the predetermined dispensing distance h between ends 18 of a tip 12 and/or 14 and element E, one or more stops 22 are provided as part of the pipette support 20. The remainder of support 20 comprises an aperture 24, which includes a keyway 26. The wall 28 of aperture 24 that is opposite to keyway 26 is constructed to receive the corresponding surface 30 of pipette 10, FIG. 4.

In accord with the invention, a key 40 is mounted onto pipette 10, FIGS. 1-4, for frictionally engaging keyway 26. Key 40 comprises a rib 42 running generally parallel to axis A, and preferably down to the bottom of lower body portion 13, as shown, although a shorter rib is also useful. Extending from rib 42 is a spring 44 constructed to press outwardly in two dimensions, the "x" dimension, FIG. 1, and the "y" dimension, FIG. 2. Most preferably, the plane of x and y is generally perpendicular to axis A. A convenient construction that achieves this arrangement is a fork spring having a Y shape. Ends 46 and 48 of the "Y", extend from a neck 49, and when free, provide a width w, in the "x" direction, FIG. 1, and a depth $d_1$ in the "y" direction, FIG. 2. Ends 46 and 48 are flexible so as to be compressible together in the x direction, FIG. 1, and so as to be bendable towards pipette body portion 13, FIG. 2.

Figure 3:
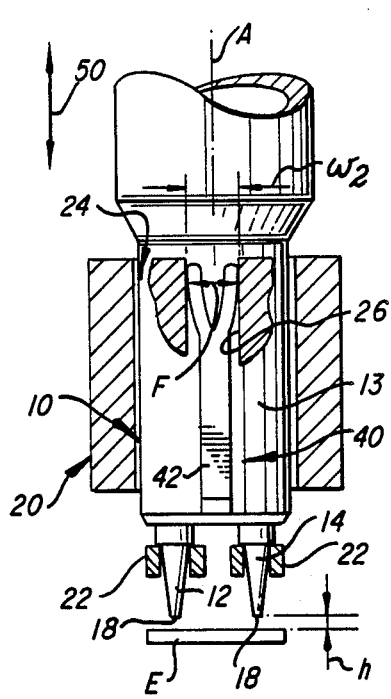
FIG. 3 is a view similar to that of FIG. 1, but illustrating the pipette in its support which is shown in section.
Figure 4:
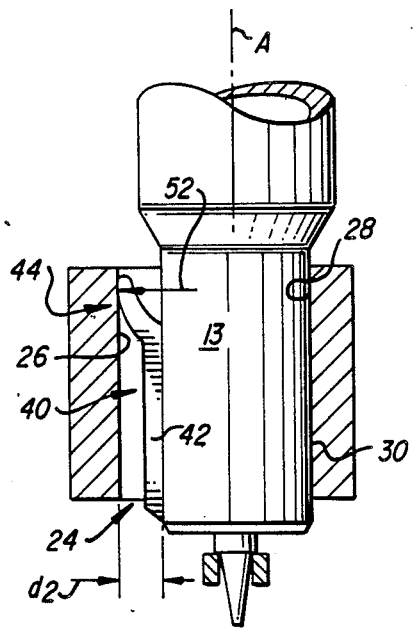
FIG. 4 is a view similar to that of FIG. 2, again illustrating the pipette in its support which is shown in section.

In use, pipette 10 is inserted into aperture 24, FIGS. 3 and 4, by moving it parallel to its axis A, lengthwise (arrow 50) through aperture 24, until stops 22 are engaged by tips 12 and 14 as shown. During this movement, spring 44 is aligned with keyway 26, and the side walls of keyway 26 cam ends 46 and 48 together to form a distance $w_2$ (that is less than $w_1$) to allow proper centering and mating engagement of spring 44 with keyway 26. In the y dimension, FIG. 4, ends 46 and 48 are pressed toward the body portion 13, so that distance $d_2$ from the body portion is less than distance $d_1$, FIG. 2. Positive engagement of the keyway by the key is thus achieved and the pipette is accurately positioned. For accurate position in the "y-y" direction, FIG. 2, the force 52 exerted by spring 42 is effective in pushing surface 30 of body portion 13 against wall 28 of aperture 24. Txe ppwsingporces exerted by ends 46 and 48, forces F, FIG. 3, act to locate it in the "x-x" direction, FIG. 1. In addition, friction forces are generated, and in microgravity or no gravity environments, such frictional engagement is effective in holding the pipette against stops 22 until the pipette is deliberately pulled out of aperture 24 against the action of such frictional forces.

Figure 5:
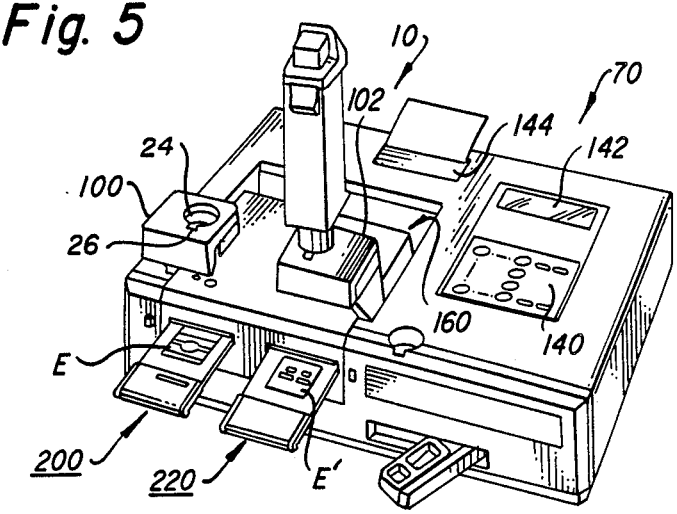
FIG. 5 is a perspective view of an analyzer with which the support and pipette are usable.

Such pipette and pipette support are useful in an analyzer 70, FIG. 5. A representative pipette 10 is shown therein, mounted "vertically" in a support 100 or 102 (102 being shown so engaged). The keyway 26 and aperture 24 are shown more clearly in support 100. In such an analyzer, test elements E or E' are pushed into dispensing stations via holders 200 or 220, and then past those stations to an incubator (not shown). A keyboard 140, visual display 142, and printer 144 are provided. Most preferably, supports 100 and 102 are pivotable so as to fit within recess 160 when not in use.

Figure 6:
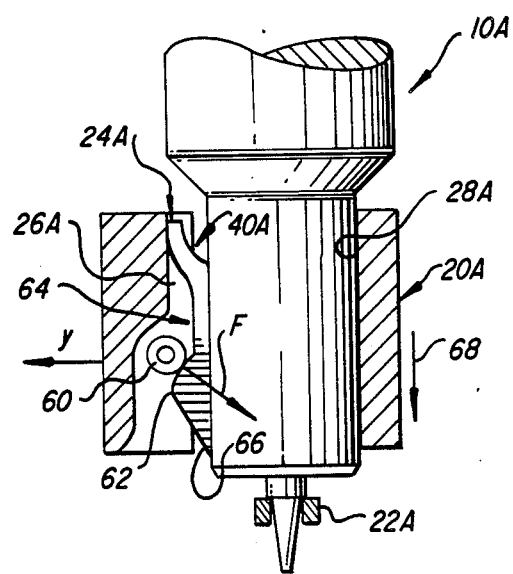
FIG. 6 is a fragmentary, partially sectional view similar to that of FIG. 4, but illustrating an alternative embodiment.

In addition, there can be provided means for releasibly pressing the pipette down against stops 22, in the event the frictional engagement force is insufficient, FIG. 6. Parts similar to those previously described bear the same reference numeral to which the distinguishing suffix "A" is appended. Thus, pipette 10A has a key 40A for engagement with a keyway 26A in support 20A, as before. In addition, however, a spring biased roller 60 is mounted in the keyway for movement in the y direction along a horizontal slot (not shown), the bias being to push roller 60 outwards towards wall 28A to the position shown. A corresponding feature of this embodiment is bump 62 formed on key 40, creating a notch 64 on the backside of bump 62. The front surface 66 of bump 62 is ramped as shown. As a result, as pipette 10A is pushed into aperture 24A, arrow 68, bump 62 cams roller 60 back until the roller drops into notch 64, where it exerts a force F on bump 62. That force, of course, includes a vertical component that keeps pipette 10A against stops 22A.

The spring means of the key need not act in both the "x" and the "y" direction one direction may be sufficient. Furthermore, it can be constructed to allow movement of the two parts together by moving in a direction perpendicular to the pipette along axis A, FIGS. 7-10. Parts similar to those described before bear the same reference numeral to which the distinguishing suffix B is appended.

Thus, pipette 10B can have a key 40B that comprises two spring arms 90, 91, FIG. 8, that extend perpendiculary to axis A from lower body portion 13B, FIGS. 7 and 8. A rib 92 projects from each arm, extending generally parallel to long axis A. The ribs connect with grasping handles 93 on the ends of the arms. Spring arms 90, 91 in turn mate with two keyways 26B formed as part of aperture 24B, FIG. 9. The lower surface 94 of each arm 90, 91, FIG. 7, is constructed to sit on stops 22B formed in the keyways, FIG. 9 and 10. The spring bias of arms 90, 91 pushes outward, arrows 95, FIG. 8, to engage arms 90, 91 with the keyway, thus creating frictional engagement only in the x x dimension. Ribs 92 slide within keyways 26B until they encounter stops 22B, FIG. 8.

Because aperture 24B is formed by walls of support 20B that are only on three sides, rather than four as in the previous embodiments, pipette 10B can be moved in and out of aperture 24B by moving it in the y direction, FIG. 10, arrows 96, by pressing handles 93 together in the x direction. Or alternatively, pipette 10B can be slid in lengthwise in a direction parallel to its long axis A.

The invention has been described in detail with particular reference to preferred embodiments thereof, but it will be understood that variations and modifications can be effected within the spirit and scope of the invention.

What is claimed is:

1. In a pipette and a support for said pipette that include a keyway on one and a mating key on the other slidable within said keyway, said support further including stop means against which said pipette is placed to dispense liquid onto a test element from a predetermined distance and location,
   the improvement wherein said key and keyway include holding means for releasably holding said key in said keyway and said pipette within said support and against said stop, to prevent accidental pipette movement that would alter said predetermined distance or location from said test element, said key comprising spring means biased to press against said keyway in two perpendicular directions so as to releasably hold said pipette against said movement by positive engagement.

2. A pipette and a pipette support as defined in claim 1, further wherein said spring is biased to press outward in only one dimension.

3. A pipette and support as defined in claim 1, further wherein said key and said spring comprise a fork spring having a Y shape, the bottom part of said "Y" shape being attached to said pipette and the upper, forked part of said shape projecting freely away from said attached bottom part with a width, when free of said keyway, that is greater than the width of said keyway to provide positive engagement of said key in said keyway.

4. A pipette and a pipette support as defined in claim 1, further wherein said spring means includes means for pressing outward in two dimensions said two dimensions defining a plane of frictional engagement.

5. A pipette and a pipette support as defined in claim 4, further wherein said plane of frictional engagement is generally perpendicular to said long axis.

6. A pipette and support as defined in claim 1, further wherein said keyway is at least as wide as said pipette and includes two opposite recesses, and said spring comprises two spring arms mounted on opposite sides of said pipette, shaped to press into said opposite recesses.

7. A pipette and support as defined in claim 6, further wherein each of said spring arms include a handle extending therefrom.

8. A pipette and pipette support as defined in claim 1, further wherein said keyway is part of an aperture in said support shaped to accommodate said pipette therein.

9. A pipette and pipette support as defined in claim 8, further wherein said pipette has a long axis, and wherein said aperture extends both parallel to said axis, and perpendicular thereto when the pipette is in use, whereby the pipette can be inserted into said aperture by moving said pipette in a direction generally parallel to, or perpendicular to, said axis.

10. A pipette and pipette support as defined in claim 8, further wherein said pipette has a long axis, and wherein said aperture extends only in a direction that is parallel to said long axis when the pipette is in use, whereby the pipette is mounted on the support by pushing it into said aperture in a direction that is generally parallel to said axis.

11. A pipette and a pipette support as defined in claim 10, wherein said improvement further includes in said keyway, means for releasably pressing on said key with a force having a component extending parallel to said long axis.

12. A pipette and a pipette support as defined in claim 1, 10, 9, or 11 further wherein said key is mounted on said pipette.

* * * * *

UNITED STATES PATENT AND TRADEMARK OFFICE
CERTIFICATE OF CORRECTION

PATENT NO. : 4,931,257
DATED : June 5, 1990
INVENTOR(S) : John A. Quenin and Johannes J. Porte It is certified that error appears in the above-identified patent and that said Letters Patent is hereby corrected as shown below:

Column 1, line 22, "and" should be --in--.

Column 1, line 37, "loose" should be --loose- --.

Column 3, line 32, "Txe ppwsingporces" should be --The opposing forces--.

Column 4, line 4, "direction one" should be --direction - one--.

Column 4, line 23, "x x" should be --x-x--.

Signed and Sealed this

Eighth Day of October, 1991

Attest:

HARRY F. MANBECK, JR.

*Attesting Officer*     *Commissioner of Patents and Trademarks*